United States Patent [19]

Hafner

[11] Patent Number: 5,333,617
[45] Date of Patent: Aug. 2, 1994

[54] CARDIAC MONITORING METHOD AND APPARATUS

[75] Inventor: Curtis R. Hafner, Cedarburg, Wis.

[73] Assignee: Marquette Electronics, Inc., Milwaukee, Wis.

[21] Appl. No.: 685,996

[22] Filed: Apr. 12, 1991

Related U.S. Application Data

[63] Continuation of Ser. No. 422,126, Oct. 16, 1989, abandoned.

[51] Int. Cl.$^5$ .............................................. A61B 51/04
[52] U.S. Cl. ....................................... 128/697; 128/903
[58] Field of Search ................. 128/419 PT, 696, 697, 128/903

[56] References Cited

U.S. PATENT DOCUMENTS

| | | | |
|---|---|---|---|
| 2,660,165 | 11/1953 | Miller | 128/696 |
| 3,646,606 | 2/1972 | Buxton et al. | 128/903 |
| 3,994,286 | 11/1976 | Svensson | 128/709 |
| 4,023,565 | 5/1977 | Ohlsson | 128/709 |
| 4,319,241 | 3/1982 | Mount | 128/903 |
| 4,550,370 | 10/1985 | Baker | 128/696 |
| 4,577,639 | 3/1986 | Simon et al. | 128/696 |
| 4,596,733 | 6/1986 | Snell et al. | 128/419 PT |
| 4,625,733 | 12/1986 | Saynajakangas | 128/903 |
| 4,658,831 | 4/1987 | Reinhard et al. | 128/903 |
| 4,681,111 | 7/1987 | Silvian | 178/697 |
| 4,742,831 | 5/1988 | Silvian | 128/696 |

OTHER PUBLICATIONS

"Telemetry Today", Electronics, Sep. 6, 1963, pp. 31-37.

Primary Examiner—William E. Kamm
Attorney, Agent, or Firm—Michael, Best & Friedrich

[57] ABSTRACT

A patient monitoring system includes a plurality of leads adapted to be coupled to a patient for generating individual ECG data voltage signals. A switching matrix couples the leads to a plurality of differential circuits for coupling selected pairs of the ECG voltage signals to each of the differential circuits for generating differential ECG vector signals functionally related to the difference between selected pairs of the ECG voltage signals. A microprocessor is coupled to the leads and to the switching matrix and is operative to reset the switching matrix to uncouple one or more first leads from the differential circuits and for coupling one or more different ones of the ECG voltage signals to differential circuit formerly coupled to receive the voltage signal from the one or more first leads. An analog to digital converter is connected to the differential means for digitizing the ECG differential signals which are stored in the microprocessor and serially supplied to a modulator for phase modulating a carrier signal to be broadcast to a receiving and displaying unit. An LCD display indicates lead failure and a low battery condition.

20 Claims, 10 Drawing Sheets

CARDIAC MONITORING METHOD AND APPARATUS

This is a continuation of U.S. application Ser. No. 07/422,126, filed Oct. 16, 1989, now abandoned.

BACKGROUND OF THE INVENTION

This invention relates to cardiac monitors and more particularly to a telemetry cardiac monitoring system.

During critical phases of cardiac illness, it is necessary to monitor a patient's physiological data, such as, heart rate, arrhythmia, the frequency of pacemaker pulses and ECG signals. In one type of patient telemetry monitoring system, a number of patients are monitored simultaneously at a central station. Such systems must provide the medical staff with continuous and reliable patient data and generally include a plurality of remote patient monitors and a central station unit coupled to the remote units by a wired data bus or by a radio frequency transmitter and receiver. If a radio system is employed, it is desirable that interference and sudden dropout be minimized. In addition, the system must not only alert the medical staff to sudden changes in the patient condition, but also partial or total system failures. Also, because telemetry nursing staffs operate under a substantial work load and the critical nature of a patient's condition, such systems now must provide accurate heart rate and arrhythmia detection in addition to continuous patient surveillance.

To provide the medical staff with usable accurate patient data, the telemetry system must first transmit and receive patient ECG data continuously and reliably. Currently available systems are not wholly satisfactory because they are prone to signal fade and drop out plus multipath distortion.

Another shortcoming of prior art telemetry systems is that only a single lead or vector of ECG data is transmitted for analysis and display. Because this limits the amount of ECG data which is processed, there is a greater tendency for incorrect classifications and false alarm. A further limitation of prior art systems is that lead failure or low battery conditions can only be determined at the central station and not at each patient location.

SUMMARY OF THE INVENTION

It is the object the invention to provide a new and improved remote cardiac monitoring method and apparatus.

Another object of the invention is to provide a remote cardiac monitoring method and apparatus which transmits data for multivector ECG analysis and display.

A further object of the invention is to provide a remote cardiac monitor transmitter which minimizes signal fade and dropout.

Still another object of the invention is to provide a cardiac monitor which permits the display of unconventional lead pair vectors.

Yet another object of the invention is to provide a remote cardiac monitor which detects and locally displays the existence of lead failures and low battery conditions at the remote patient location and transmits the same to a central station.

A still further object of the invention is to provide a remote cardiac monitor which transmits useful ECG data notwithstanding the failure of one or more patient leads.

These and other objects and advantages of the present invention will become more apparent from the detailed description thereof taken with the accompanying drawings.

In general terms the invention comprises a patient monitoring system for monitoring a patient at a location remote from a central station receiver and including signal generating means adapted to be coupled to patient for sensing individual ECG voltage signals and for generating ECG signals functionally related thereto, digitizing means coupled to the signal generating means for digitizing said ECG signals, control means coupled to the digitizing means receiving the digitized signals and for serializing the same, transmitting means including oscillator means for generating a carrier signal and phase modulating means coupled to said oscillator means for receiving the carrier signal and to said control means for receiving the serialized ECG signals and being operable to phase modulate the carrier signal with the serialized ECG signals, the transmitting means being operative to transmit the phase modulated signals to said central station receiver.

According to another of its aspects the invention comprises a method of cardiac monitoring comprising the steps of generating a plurality of voltage signals from patient leads applied to selected body locations, generating a plurality of ECG vector signals from lead couple differential voltages, digitizing the ECG signals, storing and serializing the digitized ECG vector signals, generating a carrier signal, phase modulating the carrier signal with the serialized ECG signals and transmitting the phase modulated signals to a central station receiver.

BRIEF DESCRIPTION OF THE DRAWINGS

FIGS. 10I, 10II, 10III and 10V illustrate ECG analog signals for different patient lead combinations;

DESCRIPTION OF THE PREFERRED EMBODIMENT

Figure 1:
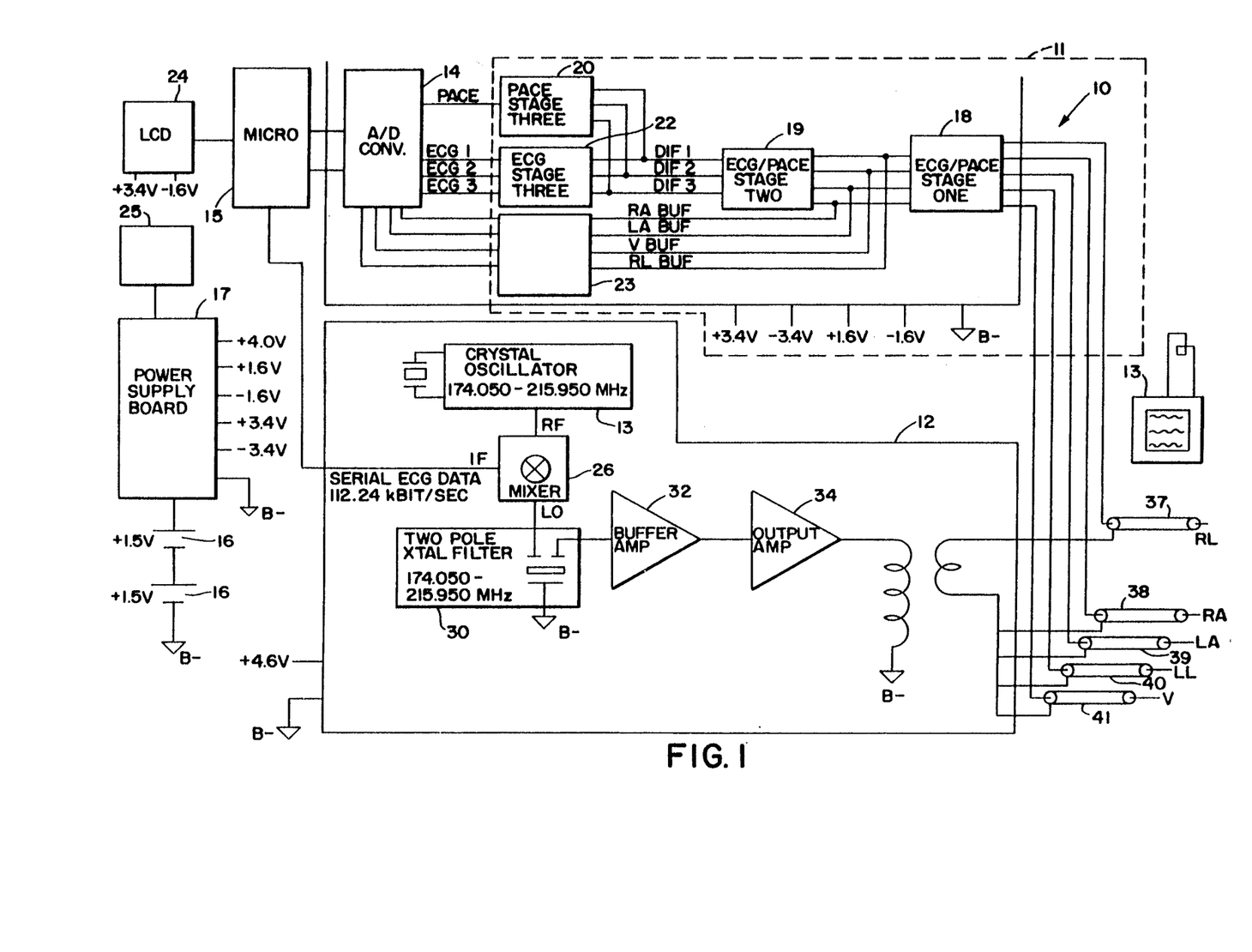
FIG. 1 is a block diagram illustrating the remote ECG monitor in accordance with the preferred embodiment of the invention.

The ECG telemetry transmitter 10 in accordance with the preferred embodiment of the invention is shown in FIG. 1 to include an ECG signal generator 11 and a transmitter 12. The ECG signal generator 11 is constructed and arranged to be coupled to a patient being monitored for receiving analog ECG voltage signals which it digitizes for phase modulating a carrier signal generated by a crystal oscillator which forms a part of the transmitter 12. The phase modulated signal is transmitted by transmitter 12 to a remote central station and receiver 13 for display and activation of alarm systems.

The ECG signal generating circuit 11 includes an analog to digital converter 14 and a microprocessor 15 which provides the transmitter 12 with a series of digital signals containing information relative to the condition of the batteries 16 of power supply 17, the existence and rate of pacemaker signals (PACE), ECG data signals as well as other control and data information. In addition, the ECG signal generating circuit 11 includes first and second input stages 18 and 19 which are common to both the ECG and pacemaker signals, a final pacemaker stage 20, a final ECG stage 22 and a coupling circuit 23.

The first input stage 18 is coupled to the patient leads RL (right leg), RA (right arm), LA (left arm), LL (left leg), and V (chest). These indicate the nominal locations to which electrodes (not shown) connected to the ends of the leads are applied. In practice, the left arm lead is applied just below the left clavicle, the right arm lead is applied just below the right clavicle, the left leg just below the rib cage on the left side, the right leg just below the rib cage on the right side and the chest is applied on or adjacent to the breast bone. The RL lead is used for ground reference purposes only and not for data transmission. When the lead wires are connected, the first input stage 18 receives ECG and pacemaker input voltage signals and is operative for sensing patient lead wire failure, buffering the lead wire inputs and protecting against voltage pulses due to electrostatic discharges and defibrillation pulses. It will be appreciated that while specific lead designations are indicated, the leads may be connected to other locations as well if desired without deviating from the invention.

Buffered output signals RABUF, LABUF, LLBUF and VBUFF from the first stage 18 are fed to the analog to digital converter 14 through the coupling circuit 23. The buffered signals from the first stage 18 are also fed to the second stage 19 where they are passed through switching matrixes and differentially amplified to provide lead couple vector voltage signals DIF1, DIF2 and DIF3. As will be discussed more fully below, the switching matrixes are controlled by the microprocessor 15 so that useful information can still be transmitted notwithstanding the failure of one or more of the patient leads. The differential signals from the second stage 19 are fed to the final pacemaker stage 20 and the final ECG stage 22.

In the final pacemaker stage 20 the differential signals DIF1, DIF2 and DIF3 are passed through a high pass filter, amplified, halfwave rectified, added and the resulting signal stretched to provide a relatively wide pacemaker detection signal PACE to the analog to digital converter 14.

The final ECG stage 22 receives the differential signals which pass through input circuits which reject the pacemaker signal. The differential signals are then passed through a high pass filter, amplified, passed through a low pass filter to the input of the analog to digital converter 14.

The analog to digital converter 14 provides digital signals to the microprocessor 15 representative of the PACE signal, the differential ECG signals and buffered ECG signals for lead failure detection. The microprocessor 15, in turn, outputs serial digital data to the transmitter 12 and controls the switching matrixes in the second input stage 19. In addition, the microprocessor 15 is coupled to a liquid crystal display (LCD) 24 which displays the conditions of the leads RA, LA, LL and V leads and the batteries 16.

The transmitter 12 comprises a digital phase modulated low power telemetry transmitter operating in the 174-216 MHz frequency band and includes a wide band balanced modulator 26 coupled to an internal oscillator 28 for receiving the main telemetry RF carrier. In addition, digital information from the microprocessor 15 is fed to the IF input of modulator 26. The LO output of modulator 26 is a mixture of the RF and IF signals along with their harmonics. This double side band signal is coupled to a band pass filter 30 which removes higher and lower order side bands, an RF buffer amplifier 32 and an RF output amplifier 34 which drives a dipole antenna consisting of shields 37, 38, 39, 40 and 41 which surround the patient leads RL, RA, LA, LL and V, respectively.

The phase modulated signals from transmitter 11 are received by the central station unit 13 which includes a RF receiver. The central station unit and receiver forms no part of the instant invention, it being sufficient to state that receiver receives the transmitted data which is processed for display and recording. In addition, the central station unit 13 will activate appropriate alarms in the event of an arrhythmia condition, a deviate heart rate and total lead failure. In addition, the central station unit will display Change Battery, RA, LA, LL or V Fail, Transmitter Fail or a TTX Mismatch Signal if the receiver receives data from a transmitter for which it is not programmed or duplicate TTX signals if two receivers are programmed to one transmitter.

Figure 2:
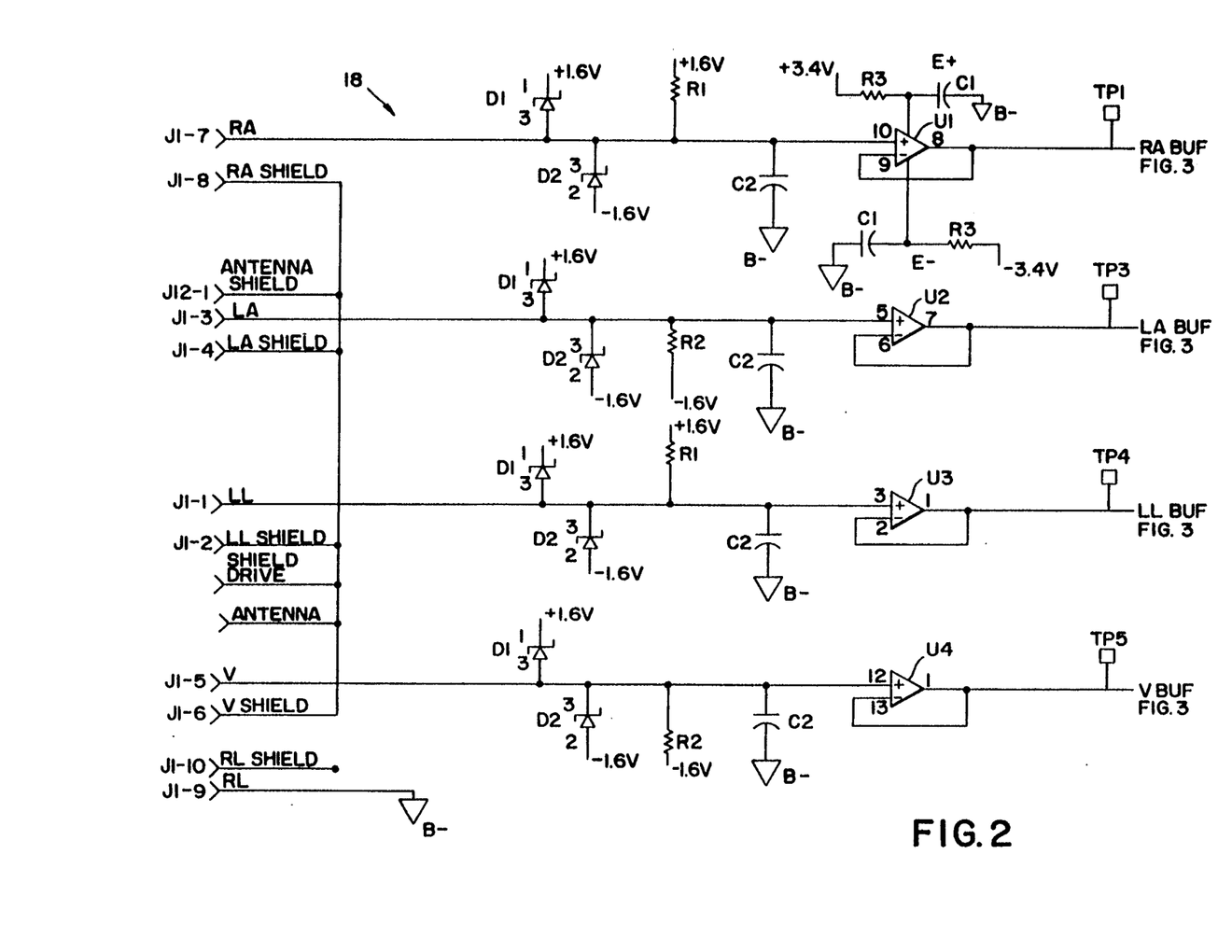
FIG. 2 schematically illustrates the first input stage of the remote monitor shown in FIG. 1.

The first input stage 18 is shown in FIG. 2 to include unity gain buffer amplifiers U1, U2, U3 and U4, respectively, connected to patient leads RA, LA, LL and V for providing buffered output voltage signals RABUF, LABUF, LLBUF and VBUF. In addition, twenty megohm resistors R1 are coupled respectively between each lead RA and LL and the +1.6 V supply and similar resistors R2 are coupled between leads LA and V and the −1.6 V supply. The resistors R1 and R2 cause the first stage outputs RABUF and LLBUF to move to +1.6 V and the outputs LABUF and VBUF to move to −1.6 V in the event there is a failure in the respective patient lead wires, such as, for example if one of the lead wires is dislodged from the patient or fails to make electrical contact. Patient lead wire failure signals are thus provided to the microprocessor 15 which, in turn, provides appropriate signals to switching matrixes U5 and U6 (FIG. 3) in the second input stage 19 and to the LCD display 24 as will be discussed more fully below. In addition, low leakage diodes D1 and D2 are connected respectively between each patient lead RA, LA, LL and V and the ±1.6 V power supply to protect the circuit from electrostatic discharges and defibrillation pulses. Each buffer amplifier U1, U2, U3 and U4 is powered by the ±3.4 volt supply E+, E− through resistors R3 and capacitors C1 and each lead is coupled to the return by a capacitor C2, as shown in connection with lead RA. Buffer amplifiers U2, U3 and U4 are also powered by the supplies E+, E− but these connections are omitted from the drawings for the sake of brevity. Other portions of the signal generator 11 include identical power supply circuitry which are also identified by the reference E+, E−.

Figure 3:
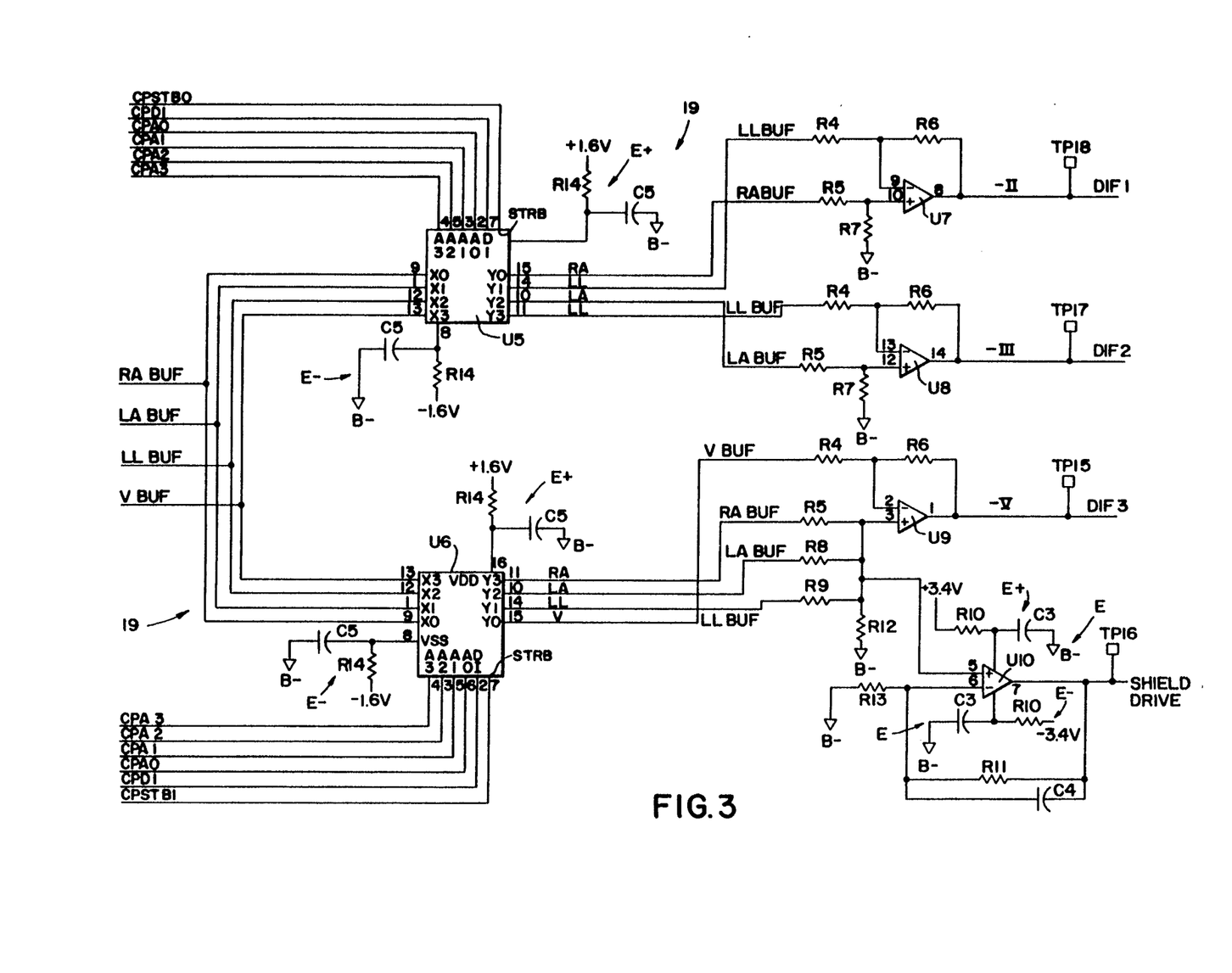
FIG. 3 schematically illustrates the second input stage of the remote monitor illustrated in FIG. 1.

FIG. 3 shows the second input stage to include switch matrixes U5 and U6, each connected to receive the signals RABUF, LABUF, LLBUF and VBUF from the first stage 18 at input terminals X0, X1, X2, and X3, respectively. In addition, control terminals A0, A1, A2, A3, D1 and S of each switching matrix U5 and U6 are connected to the microprocessor 15 for receiving control signals. The output signals from the switching matrixes U5 and U6 are provided to the inputs of differential amplifiers U7, U8, U9 and U10. When all of the leads are good, signals RABUF and LABUF are provided to differential amplifier U7, signals LABUF and LLBUF are provided to differential amplifier U8, signals RABUF, LABUF, LLBUF and VBUF are provided to differential amplifier U9. Each of the differential amplifiers U7, U8 and U9 have identical input resistors R4 and R5, feedback resistors R6 and biasing resistors R7 and each amplifies the difference between the input signals to provide lead couple vector signals DIF1, DIF2 and DIF3, which are the input signals to the final pacemaker stage 20 and the final ECG stage 22.

The switching matrixes U5 and U6 are operative in response to control signals received from the microprocessor 15 for setting internal switches so that useful information will be provided to the microprocessor 15 notwithstanding lead failures. The following table shows the switching connections for various lead conditions:

TABLE 1

| RA | LA | LL | V | DIF 1 | DIF 2 | DIF 3 |
|----|----|----|----|-------|-------|-------|
| 0 | 0 | 0 | 0 | II | III | V |
| 0 | 0 | 0 | 1 | II | III | I |
| 0 | 0 | 1 | 0 | I | I | I |
| 0 | 0 | 1 | 1 | I | I | I |
| 0 | 1 | 0 | 0 | II | II | II |
| 0 | 1 | 0 | 1 | II | II | II |
| 1 | 0 | 0 | 0 | III | III | III |
| 1 | 0 | 0 | 1 | III | III | III |
| All Other | | | | II | III | V |

Where:
1 = Failed lead;
0 = Good lead;
I = a(LABUF − RABUF);
II = a(LLBUF − RABUF);
III = a(LLBUF − LABUF);
V = a[VBUF − (RABUF + LABUF − LLBUF) /3]; and
a = the amplification factor for U7, U8 and U9.

It can be seen from Table 1 for example, that if lead V fails, the inputs to amplifiers U7 and U8 will remain unchanged but that amplifier U9 will receive signals RABUF and LABUF instead of RABUF and VBUF. Since the "All Other" combinations of lead failures will provide invalid information, this will be sensed by the microprocessor which will generate an appropriate signal indicating the useful information is not being transmitted.

Those skilled in the art will appreciate that the lead combinations listed in the event of a lead failure are merely examples and that other combinations are also possible.

The signals RABUF, LABUF and LLBUF are applied to the noninverting terminal of operational amplifier U10 through input resistors R5, R7 and R8 to provide an input voltage which is the average of these signals and a reference signal for providing a differential output signal SD which is the shield drive for the commonly connected conductor shields as shown in FIG. 2. By using the average of the lead signals, the capacitance effect between the shields and the patient conductors is cancelled in the shield drive signal.

Each of the differential amplifiers U7, U8 and U9 is powered by the plus or minus 3.4 V supply Circuit E+, E− as shown in connection amplifier U10. In addition, capacitor C4 is shown connected in parallel with the feedback resistor R11 of amplifier U10 to provide a low pass filter. Switching matrixes U5 and U6 are powered from the plus or minus 1.6 V supply through resistors R14 and capacitors C5 as shown.

Figure 4:
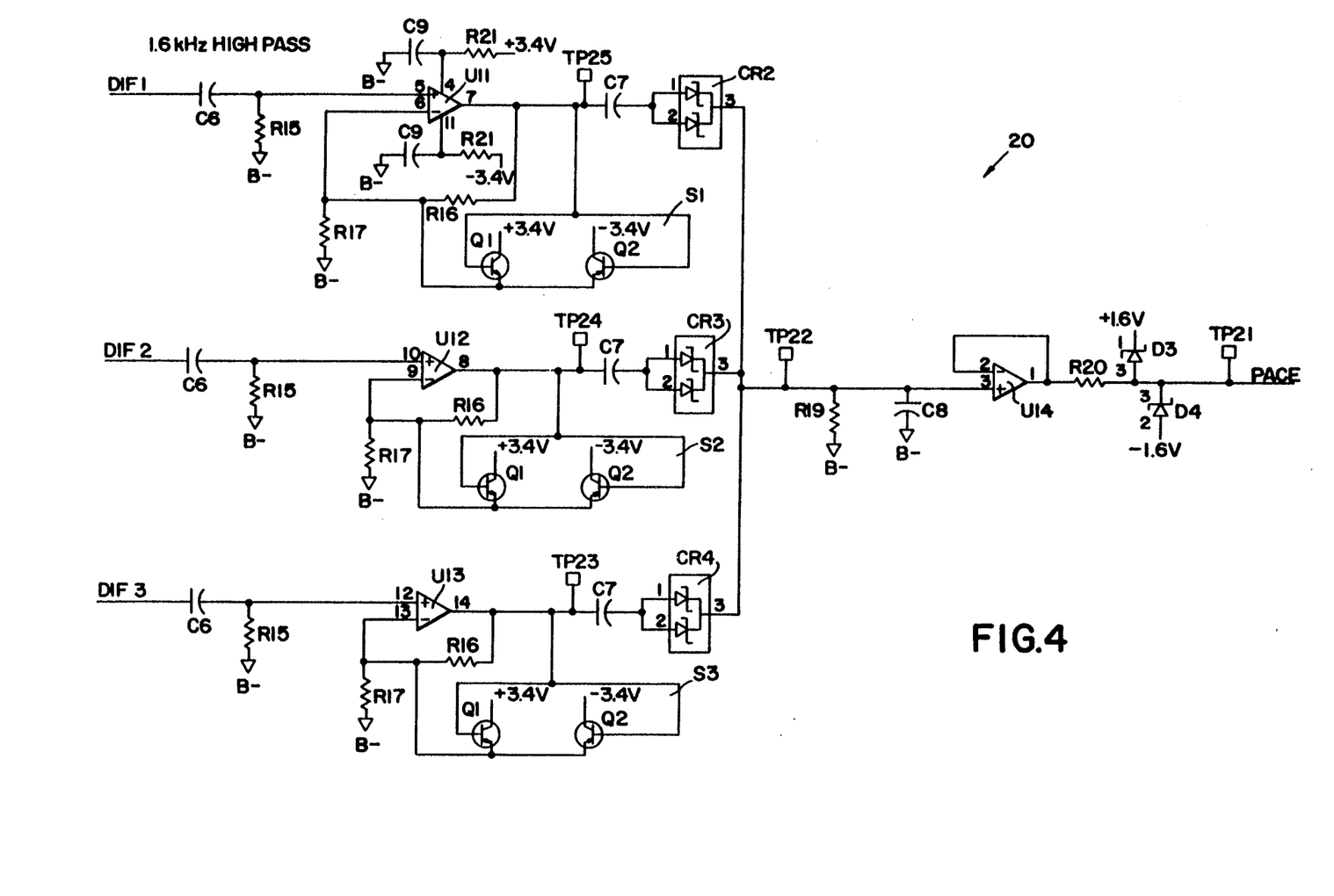
FIG. 4 schematically illustrates the final pacemaker stage of the remote monitor shown in FIG. 1.

The final pacemaker stage 20 is shown in FIG. 4 to include amplifiers U11, U12 and U13 which amplify the signals DIF1, DIF2 and DIF3, respectively. Each amplifier U11, U12 and U13 is proceeded by a 1.6 KHz high pass filter consisting of a capacitor C6 and a resistor R15. Slew limiting circuits S1, S2 and S3 are respectively connected to amplifiers U11, U12 and U13 and each consists of transistors Q1 and Q2 and are operative to prevent saturation of the amplifier output voltages. In particular, the base of each transistor Q1 and Q2 is connected to the output of amplifier U11, for example, and their collectors are connected to the junction between feedback resistor R16 and resistor R17. In the event of a voltage surge resulting from a pacemaker pulse, one of the transistors Q1 or Q2 may become conductive, depending upon whether the pulse is either positive or negative. This will shunt the feedback signal so that the gain of the amplifier will be reduced.

The amplifiers U11, U12 and U13 are coupled to halfwave rectifier CR2, CR3 and CR4, respectively, through coupling capacitors C7 so that the amplifier output signals are rectified. The sum of the rectified voltage signals is provided to a pulse stretching circuit consisting of resistor R19 and capacitor C8 to provide a wide pacemaker detect pulse which can be sampled by the analog digital converter 14. The pacemaker detect signal is passed through unity gain buffer amplifier U14 and output resistor R20 to the analog digital converter 14. Diodes D3 and D4 are Schottky diodes which clamp the amplifier U14 output signal with respect to the plus or minus 1.6 V reference.

Figure 5:
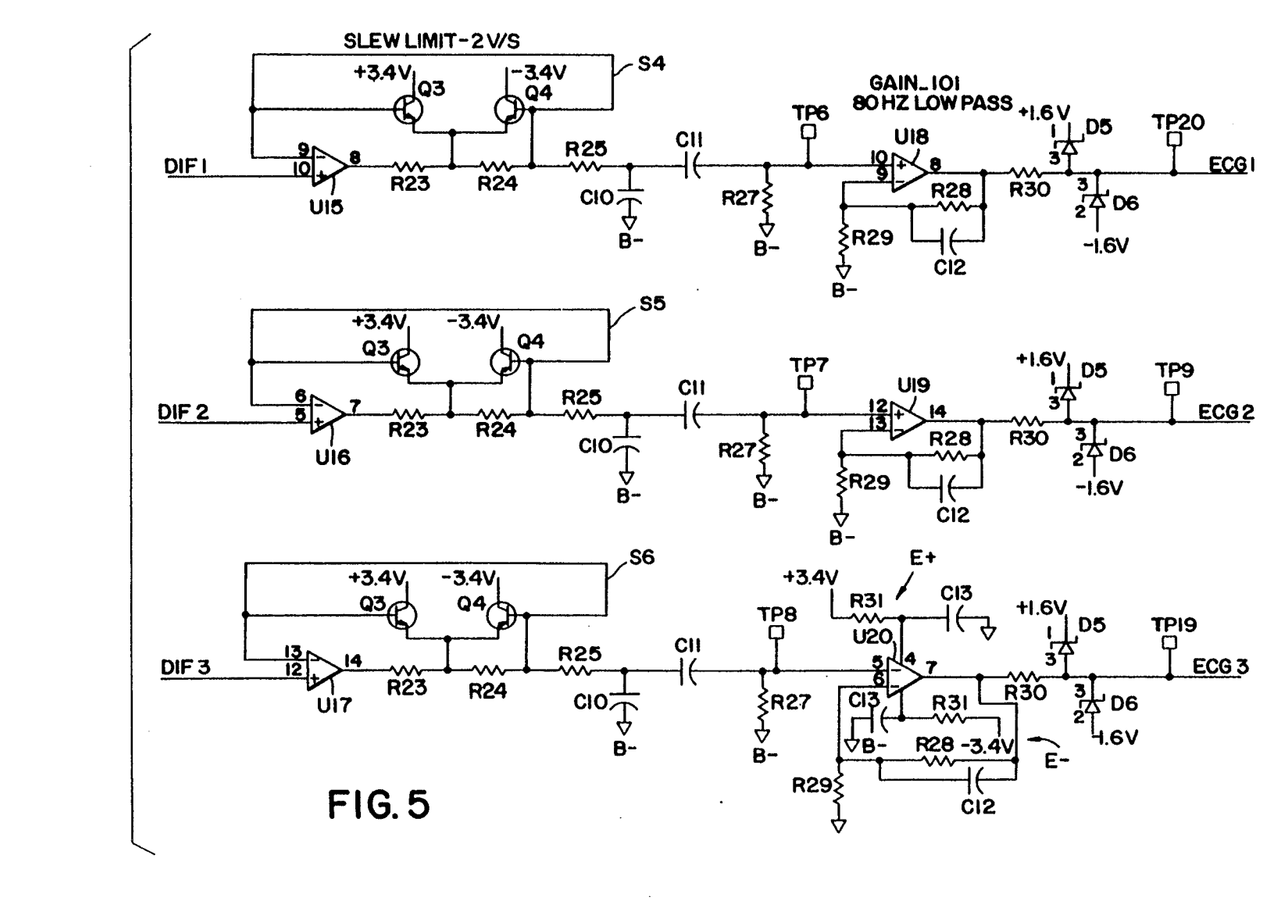
FIG. 5 schematically illustrates the final ECG stage of the remote monitor shown in FIG. 1.

The final ECG stage 22 as shown in FIG. 5 to include operational amplifiers U15, U16 and U17, each of which is coupled to receive the differential signals DIF1, DIF2 and DIF3, respectively at their noninverting inputs. In addition, slew limiting circuits S4, S5 and S6, each consisting of transistors Q3 and Q4, are coupled to amplifiers U15, U16 and U17, respectively, and each has a slew rate of two volts per second so as to limit rapid voltage changes when the amplifiers sees the pacemaker pulse. More particularly, the output signals from amplifiers U15, U16 and U17 are applied to output resistors R23 and R24. In the event of a voltage rise in excess of two volts per second, one of the transistors Q1 or Q2, depending upon the sign of the signal, will become conductive to shunt a portion of the feedback signal thereby reducing the gain of the amplifier. Resistor R25 and capacitor C10 limit the instantaneous current flow from each amplifier to limit the slew rate.

The output signals from amplifiers U15, U16 and U17 are respectively passed to high gain amplifiers U18, U19 and U20 through 2.4 Hz high pass filters consisting of capacitors C11 and resistors R27. In addition, an eighty Hz low pass filter consisting of capacitor C12 shunts the feedback resistor R28 and resistor R29 to the return. The outputs of the amplifiers U18, U19 and U20 are passed through resistors R30 to the analog digital converter 14. Schottky diodes D5 and D6 clamp each of the output signals with respect to the plus or minus 1.6 V supply. The total gain of the amplifiers U18, U19 and U20 is 101 and there is a 3.16 gain in the second stage for a total gain of 319 whereby the maximum input signal of plus or minus 5 MV provides an output to the analog digital converter of plus or minus 1.6 V. Each of the amplifiers U15–U20 are powered from the plus or minus 3.4 V by power supply circuits E+, E−, although only one power supply E+, E− is shown in connection with amplifier U20.

Figure 6:
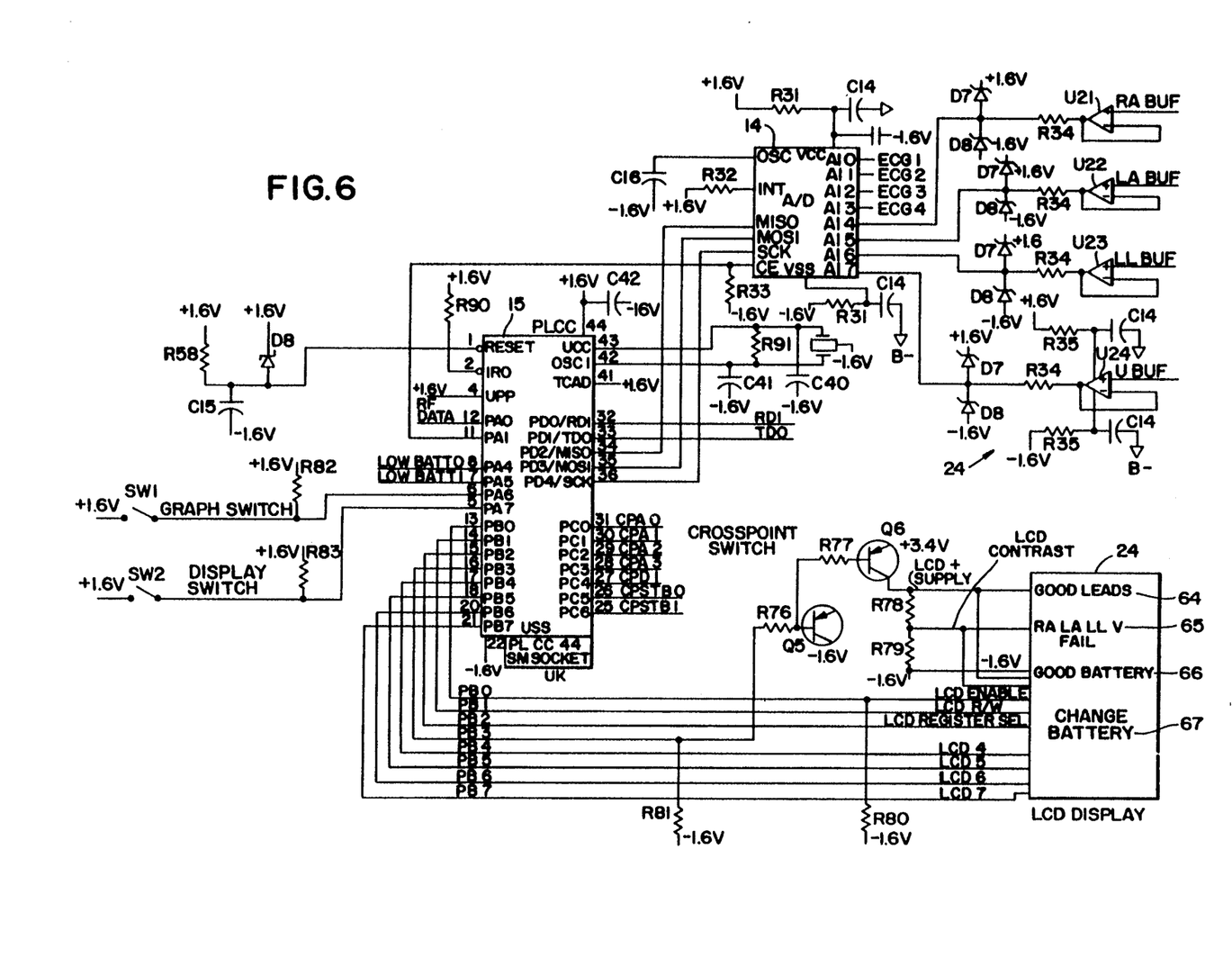
FIG. 6 schematically illustrates the connections of the analog/digital converter and microprocessor of the remote monitor shown in FIG. 1.

The analog to digital converter 14 is connected to the final ECG stage for receiving the ECG 1, ECG2 and ECG3 signals at ports A10–A12. The PACE signal from the final pacemaker stage 20 is received by the analog digital converter 14 at port A13. Lastly, the buffered signals from the first ECG stage 18 are coupled to ports A14–A17 of digital to analog converter 14 through circuit 24 which consists of unity gain buffer amplifiers U21, U22, U23 and U24. The output of unity gain buffer amplifiers U21–U24 are respectively coupled to the digital to analog converter ports through resistors R34. Diodes D7 and D8 clamp each of the input signals to the digital to analog converter with respect to the plus or minus 1.6 V supply. In addition, each of the buffer amplifiers U21–U24 are powered from the plus or minus 3.4 V supply by power supply circuit E+, E−, although only one such circuit is shown in connection with amplifier U24.

The analog to digital converter 14 shown in FIG. 6 digitizes the ECG1, ECG2 and ECG3 signals from the final ECG stage 22, the PACE signal from the final pacemaker stage 20 and the RABUF, LABUF, LLBUF and VBUF signals from the first stage 18. While any suitable analog to digital converter may be employed, one example that has been used successfully is the RCA Model 68HC68. The analog to digital converter 14 is driven from the plus or minus 1.6 V power supply through capacitors C14 and resistor R31, as shown.

The microprocessor may be an 8-bit, single chip microcomputer containing an on chip oscillator, a central processing unit, an arithmetic logic unit, a random access memory, read only memory, a I/O bidirectional serial interface system and a timer. One such microprocessor which may be employed is the Motorola model MC68HC705. The analog to digital converter 14 converts three channels of analog ECG patient data, the pacemaker monitor signal PACE and the RABUF, LABUF, LLBUF and VBUF patient lead status signals to 10-bit digital data which is stored in the microprocessor 15 and serially transmitted, to the IF terminal of the modulator 26. In the event of a patient lead failure, the microprocessor 15 provides control signals to the switching matrixes U5 and U6 through ports PC0-PC6 whereby the switching operations discussed above will be implemented. The A/D chip enable signal from microprocessor 15 is provided through port PA1; control signals to the A/D converter are provided through port PD3 to port MOS1 and serial clock signals are provided to the A/D converter from port PD4 to port SCK. Battery status signals are provided to ports PA3 and PA4 of the microprocessor 15 from the power supply circuit as will be discussed more fully below.

Switches SW1 and SW2 are operative to provide voltage signals to ports PA6 and PA7 for activating the display and graph of the remote unit 13 (FIG. 1) and the LCD display through ports PB0-PB7 to indicate battery status and lead failures, respectively. The external clock for the microprocessor 15 comprises a 2.4576 MHz crystal Y1 coupled to the OSC1 and OSC2 terminals.

Figure 7:
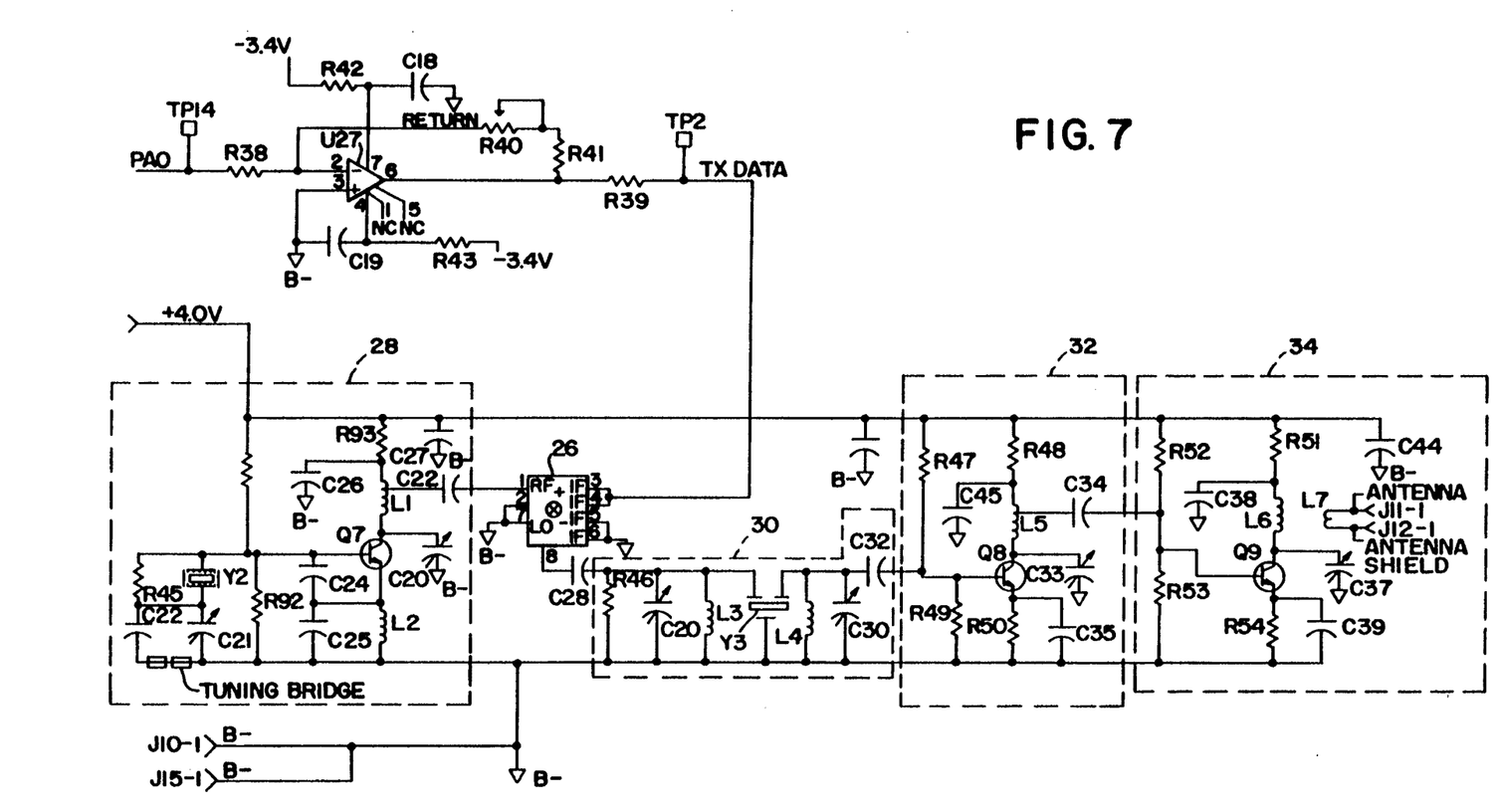
FIG. 7 schematically illustrates the transmitter portion of the remote monitor shown in FIG. 1.

As shown in FIG. 7, the microprocessor output data from port PA0 is coupled to the IF input of modulator 26 by an IF drive circuit 50 consisting of a unit gain buffer amplifier U26 whose inverting input is coupled to port PA0 by an input resistor R38 and whose output is coupled to the IF input by output resistor R39. In addition, amplifier U26 includes feedback resistors R40 and R41 and is powered from the plus or minus 3.4 V source through resistors R42 and R43 and capacitors C18 and C19. Data from the microprocessor 15 in the form of plus or minus square wave voltage signals of approximately 2.4 V is provided to the modulator 26 of the transmitter 12 as illustrated in FIG. 7. These represent binary 1 and 0 digits. Modulator 26 mixes the data signals from the microprocessor 15 with a RF carrier signal.

A balanced mixer 26 is used to produce bi-phase-shift-keyed (BPSK) modulation is used within the coherent digital telemetry transmitter to transmit patients psychological data (ECG, etc.) generated by the microprocessor into a phase modulated RF carrier. The RF output of the modulator drives a dipole antenna formed by the shields of the patient lead wires. A modified Colpitts oscillator 28 is coupled to the modulator 26 for generating the main telemetry channel CW carrier. Oscillator 28 includes a series resonant ninth overtone crystal Y2 and a switching transistor Q7 having its collector connected to an LC circuit consisting of inductor L1 and capacitor C20. When the crystal Y2 is oscillating, an AC voltage is applied to the base of transistor Q7 causing the LC circuit L1, C20 to oscillate. This in turn provides an oscillating feedback voltage to the crystal Y2 resulting in sustained oscillation at the ninth overtone of the crystal Y2 which is the final telemetry channel frequency. Variable capacitor C21 is used to tune the oscillator frequency to within plus or minus 300 HZ of the channel frequency. The oscillator 28 is coupled to the RF input of the frequency modulator by coupling capacitor C22.

The modulator 26 is a wide band 1–500 MHz balanced mixer. While any suitable mixer may be employed, the Mini Circuits Model SBL-1 has been found to operate satisfactorily, The RF carrier signal from the oscillator 28 is applied to pin 1 and digital information from the microprocessor 15 is applied to the IF input (pins 3 and 4). The LO output is now the mixed combination of the two signals along with their harmonics. For example, where a binary 1 is received at the IF input, the carrier signal is phase shifted plus 180° and when a binary O is received, the carrier signal is phase shifted zero degrees. This double side band signal has a carrier suppression of approximately 20 dB. The amount of insertion loss in carrier suppression is proportional to the amount of drive current supplied by microprocessor 15.

The phase modulated signal is passed through coupling capacitor C28 to the band pass filter 30 for attenuating unwanted harmonics and to reduce the possibility of adjacent channel interference with other receivers in the system. The band pass filter 30 includes a two pole crystal Y3, inductors L3 and L4, capacitors C29 and C30 and resistor R46. Capacitors C29 and C30 optimize filter performance providing minimum insertion loss and flat response across the pass band. Filter 30 is coupled to the buffer amplifier 32 by a coupling capacitor C32.

Buffer amplifier 32 includes a transistor Q8 whose base is connected to coupling capacitor C32 and whose collector is connected to an LC bridge consisting of inductor L5 and tuning capacitor C33. The RF buffer amplifier is tuned with capacitor C33 to a specific output level and this output signal is coupled to the output amplifier 34 by a coupling capacitor C34.

The output amplifier 34 includes a transistor Q9 whose base is coupled to capacitor C34 and whose collector is connected to the dipole antenna formed by the patient conductor shields through inductor L6 and coupling inductor L7. Also, connected to the transistor Q9 collector is tuning capacitor C37. This power amplifier operates in the 174 to 216 MHZ frequency band and drives the dipole antenna formed by the shields of the patient lead wires. Capacitor C37 tunes amplifier 34 to a specific output level and the output signal is coupled to the antenna through a one turn coupling link L7.

The power supply 17 is conventional and will not be discussed in detail for the sake of brevity. It is sufficient for purposes of understanding the invention to state that the power supply includes charge pumps and voltage regulators which convert the battery voltage into plus or minus 3.4 V, plus or minus 1.6 volts and plus 4 volts as required to drive to ECG signal generator 11 and the transmitter 12.

Figures 8, 9, 10A, 10B, 10C, 10D:
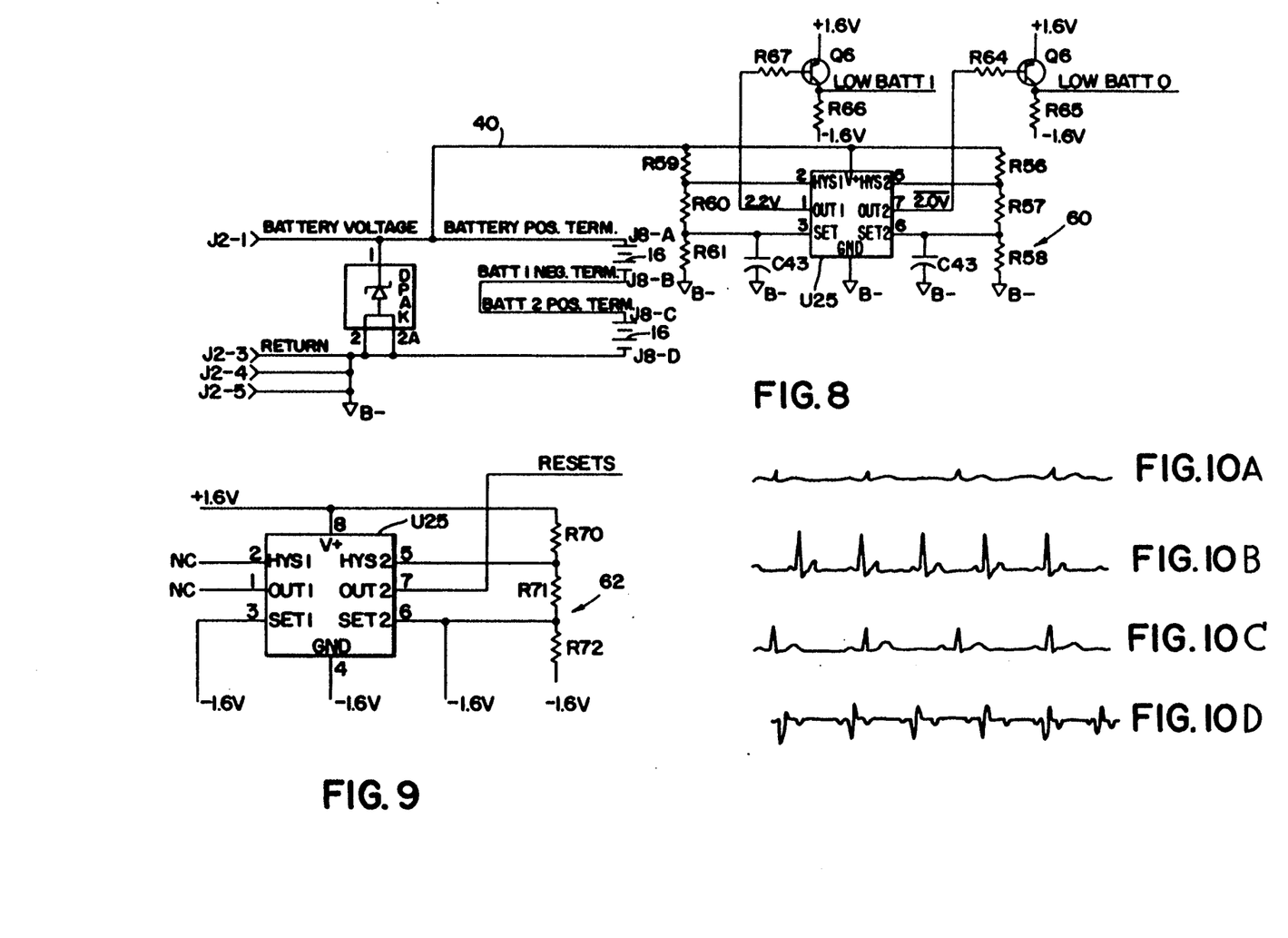
FIG. 8 schematically illustrates the low battery detection circuit of the remote monitor shown in FIG. 1.
FIG. 9 schematically illustrates the microprocessor reset circuit of the signal generator portion of the remote monitor shown in FIG. 1.

FIGS. 8 and 9 shows the low battery detection circuit 60 and microprocessor reset circuit 62 which form a part of the power supply 17 and which include level detectors U25 and U26. While any suitable level detectors may be employed, RCA Model Nos. ICL 7665 have been used successfully. Low battery detection circuit 60 includes a pair of resistance bridges R56, R57, R58 and R59, R60, R61 connected between the positive battery terminal and the return. The input terminals HYS1 and HYS2 of level detector are respectively connected to the resistor R59, R60 junction and the R56, R57 resistor junction, respectively. The level detector U25 is constructed and arranged to provide an output signal from outlet 1 terminal when the battery voltage falls to 2.2 volts and an output signal from output 2 terminal when battery voltage falls to 2.0 volts. The set 1 and set 2 terminals of U25 are respectively connected to the R60, R61 resistor junction and the R57, R58 resistor junction respectively. The output 1 terminal is connected to the base of a transistor Q9 through resistor R67 and the output 2 terminal is connected to the base of transistor Q10 through resistor R64. When the battery voltage falls to 2.2 volts, a gate signal will be provided to transistor Q9 which will cut off the collector current flowing through resistor R66. This provides a low battery 1 signal (logic "0") to microprocessor port PA4. Similarly, level detector U25 is operative to provide an output signal at output 2 when battery voltage falls below 2.0 volts to remove the gate signal to transistor Q9. This causes transistor Q9 to become conductive and pass collector current through resistor R65 thereby providing a low battery 0 signal (logic "1") to microprocessor port PA5. The microprocessor then provides signals through ports PB0-PB7 to actuate the LCD display so that the appropriate low battery indication is made. U25 is powered directly from the battery voltages indicated.

The microprocessor reset circuit 62 is shown in FIG. 9 to include level detector U26 and a resistance network consisting of resistors R70, R71 and R72. The HYS2 input of the level detector U26 is connected to the R71, R72 junction, the set 2 input is connected to the resistor R70, R71 junction and U26 is driven by plus or minus 1.6 volt supply. If the plus or minus 1.6 volt supply, which also powers the microprocessor 15, goes low, level detector U26 will provide a reset signal from output 2 to the microprocessor 15. This will inhibit the microprocessor until the supply returns to plus or minus 1.6 volts.

Referring again to FIG. 6, graph switch SW1 and display switch SW2 are shown to be connected to microprocessor parts PA6 and PA7, respectively. The closing of switch SW1 causes the ECG graphs to be displayed and recorded at the remote central station 13. Closing switch SW2 activates the LCD display 24.

LCD display 24 is connected to microprocessor ports PB0-PB9. Port PB3 is connected to the gate of transistor Q5 through resistor R76. The emitter of Q5 is connected through resistor R77 to the gate of Q6. When switch SW2 is closed, a gate signal from microprocessor port PB3 causes Q6 to become conductive and provide power and a contrast signal to LCD display 24 through resistors R78 and R79.

The LCD display 24 includes displays 64 and 65 which respectively indicate the conditions of leads RA, LA, LL and V and displays 66 and 67 which indicate the condition of the battery 16. When switch SW2 is closed, the microprocessor will provide an appropriate signal to the LCD display 24 to energize the appropriate portions of the displays 64 or 65 to indicate whether the leads are good or which of the leads, if any, is if all of the leads are good, display 64 bad. For example, will be energized. On the other hand, if one or more of the leads have failed, the appropriate portion of display 65 will be energized. In addition, the display 67 will be energized if a low battery condition exists. If battery voltage greater than 2.2 volts, display 66 will be energized as an indicated that the batteries are good. In this manner, the hospital staff can determine at the patient location the condition of the leads and the batteries without the necessity to travel to the central station.

FIGS. 10I, 10II, 10III and 10V show plots of the ECG vector signals. FIG. 10I is the left arm and right arm lead pair vector; FIG. 10II is the left leg and right arm lead pair vector; FIG. 10III is the left leg and left arm lead pair vector; and FIG. 10V is the chest and LA, LA, LL lead pair vector. When all leads are good, each of these graphs would be displayed at the central station unit 13. However, if one or more of the leads are bad, Table 1 illustrates the graphs which would be displayed. The existence of a pacemaker signal would be displayed at the central station unit by alphanumerics.

Phase shifting the carrier signal provides superior bit error rate performance over other systems. Furthermore, by transmitting the ECG data from four lead pairs, greater arrhythmia detection and alarm accuracy can be achieved and useful information can be transmitted even in the event that one or more leads should fail. Furthermore, the hospital staff can monitor low battery conditions and lead failures at the remote patient location without the need to return to the central station.

Figure 11:
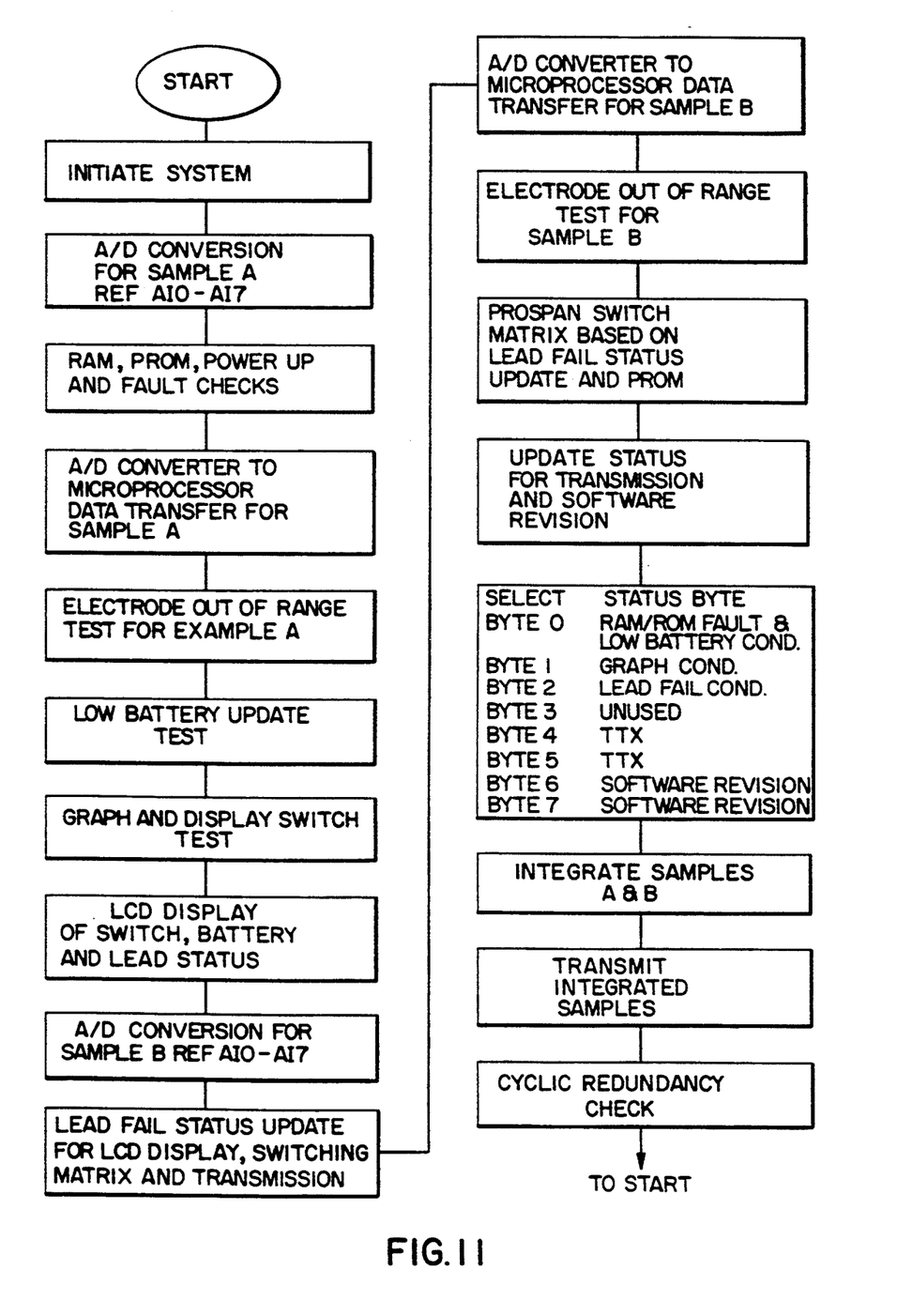
FIG. 11 is a flow diagram showing the microprocessor program usable with the remote ECG monitor according to the invention.

FIG. 11 shows the program sequence for the microprocessor. The switching matrix program sets the switching matrixes U5 and U6 to provide the desired lead couples. For example, the microprocessor may be programmed to set the switching matrixes so that the desired classical lead couple pairs II, III and V. On the other hand non-classical lead couple vectors can be selected for transmission and display. It will be appreciated that the physician may desire lead vector combinations other than those set forth in Table 1. For this reason, the microprocessor 15 preferably is programmable to provide other than the classical lead couple combinations, in which event the table of lead couple combinations in the event of lead failure would, of course, be different than that set forth in Table 1. It will also be appreciated that the lead couple combinations in Table 1 are not exclusive and that other combinations are possible in the event one or more leads should fail and this is true regardless of whether classical or non-classical lead couples are being transmitted.

The A and B data samples are taken at the rate of 40 HZ each so that the integrated samples have a sample rate of 120 HZ which insures a high degree of accuracy and reduces signal noise.

Figure 12:
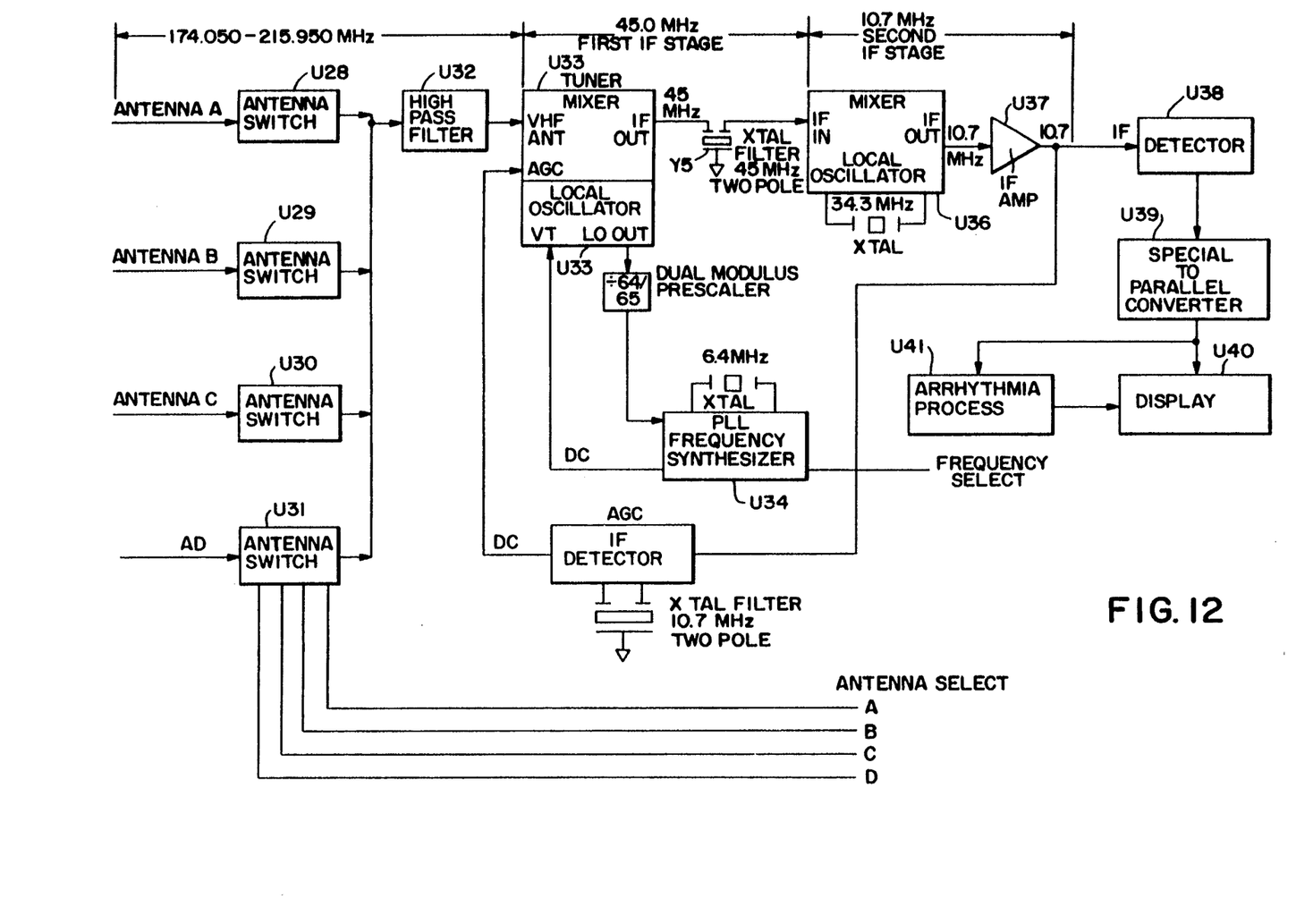
FIG. 12 is a block diagram illustrating a central station usable with the remote monitor according to the invention.

The remote central station and receiver 13 shown in FIG. 12 forms no part of the present invention and accordingly will only be described in general terms for sake of brevity. It will be sufficient for purposes of understanding the invention to state that the receiver 13 is preferably a VHF tuner capable of being tuned to the frequency band of the transmitter 12 which in the preferred embodiment is 174–216 MHz. In addition, it is desirable that the receiver 13 be capable of selecting the strongest RF signal from a choice of four different antenna systems by means of RF switches U28, U29, U30 and U31. The output of the RF switches is passed through a high pass filter U32 into the VHF antennae input of a VHF/UHF tuner U33 which comprises a first intermediate frequency (IF) stage. The first IF stage includes a local oscillator U33 and down converts the received 174–216 MHz VHF signal to 45 MHz. The frequency of the local oscillator U33 is set and locked by a programmable, serial input phase locked loop frequency synthesizer U34.

The frequency synthesizer U34 is preferably a programmable frequency synthesizer which is programmed by a clocked nineteen bit serial data stream input generated by an external microprocessor circuit (not shown). The microprocessor circuit, under software control, is programmed with the channel frequency assigned to the particular receiver assembly. The frequency synthesizer U34 includes a reference oscillator, a selectable reference divider, a digit phase detector, a ten bit programmable divide by N counter, a seven bit programmable divide by A counter and shift register and latch circuitry for accepting a serial data input. The local oscillator U33 runs 45 MHz above the desired carrier frequency (high-side mixing) and the step resolution is 50 KHz. The 45 MHz IF output is passed to the second IF stage U35 through a two pole crystal bypass filter Y5 to eliminate unwanted frequency mixing products.

The PLL frequency synthesizer U34 compares a reference frequency with the LO output of the local oscillator U33 which is passed through a dual modulus prescaler U37 and a 6.4 MHz reference frequency generated by crystal Y4. The error signal locks the tuners local oscillator U33 to the desired frequency.

The second intermediate frequency (IF) stage U36 down converts the 45 MHz first stage IF signal to 10.7 MHz. In particular, the 45 MHz signal from the first stage is mixed in the second IF stage with 34.3 MHz from the second stage local oscillator U35 to provide 10.7 MHz. The second IF stage output is amplified by U36 and is used by the first IF stage to provide a single strength indication for the automatic gain control operation and for external IF detection.

The amplified 10.7 MHz signal is passed to a detector U38 which converts the frequency signal to serial digital data. This information is converted by a serial to parallel convertor and then provided directly to the display U40 and through an arrhythmia processor U41.

The following is a component list for the elements illustrated in the drawings, it being understood that these are mere examples and are disclosed to assist those skilled in the art in practicing the invention and that there is no intention to limit the invention to the specifically disclosed components. It will also be appreciated by those skilled in the art that equivalent components and circuit subsystems can be substituted without deviating from the scope of the invention.

COMPONENT LISTING

| | | | | | |
|---|---|---|---|---|---|
| C1 | 0.1 UF | L1 | Coil TN 3T | R50 | 510 |
| C2 | 22 PF | L2 | 1 UH | R51 | 2.7K |
| C3 | 0.1 UF | L3 | 22 NH | R52 | 120K |
| C4 | 1000 PF | L4 | 33 NH | R53 | 51K |
| C5 | 0.1 UF | L5 | Coil TN 4T | R54 | 100 |
| C6 | 1000 PF | L6 | Coil 3T | R56 | 10.0K |
| C7 | 0.15 UF | L7 | Coil 1T | R57 | 100K |
| C8 | 0.01 UF | Q1 | MMBT 3904 | R58 | 200K |
| C9 | 0.1 UF | Q2 | MMBT 3906 | R59 | 2.00K |
| C10 | 0.15 UF | Q3 | MMBT 3904 | R60 | 20.0K |
| C11 | 0.15 UF | Q4 | MMBT 3906 | R61 | 32.4K |
| C12 | 0.01 UF | Q5 | MMBT 3904 | R64 | 100K |
| C13 | 0.1 UF | Q6 | MMBT 3906 | R65 | 100K |
| C14 | 0.1 UF | Q7 | 5179 | R66 | 100K |
| C15 | 0.1 UF | Q8 | 5031 | R67 | 100K |
| C16 | 68 PF | Q9 | 5031 | R70 | 2.00K |
| C18 | 0.1 UF | R1 | 20M | R71 | 100K |
| C19 | 0.1 UF | R2 | 20M | R72 | 78.70K |
| C20 | 5-25 PF | R3 | 2.00K | R76 | 100K |
| C21 | 5-25 PF | R4 | 78.70K | R77 | 100K |
| C22 | 47 PF FIG. 7 | R5 | 78.70K | R78 | 100K |
| C23 | 5 PF | R6 | 249.0K | R79 | 2.00K |
| C24 | 20 PF | R7 | 249.0K | R80 | 100K |
| C25 | 27 PF | R8 | 78.70K | R81 | 100K |
| C26 | 1000 PF | R9 | 78.70K | R82 | 100K |
| C27 | 1000 PF | R10 | 47 | R83 | 100K |
| C28 | 10 PF | R11 | 10.0K | R90 | 100K |
| C29 | 5-25 PF | R12 | 83.00K | R91 | 10M |
| C30 | 5-25 PF | R13 | 32.4K | R92 | 100K |
| C32 | 5 PF | R14 | 47 | R93 | 103K |
| C33 | 5-25 PF | R15 | 100K | U1 | TLC27L9 |
| C34 | 1000 PF | R16 | 200K | U2 | TLC27L9 |
| C35 | 100 PF | R17 | 2.00K | U3 | TLC27L9 |
| C37 | 5-25 PF | R19 | 1.82M | U4 | TLC27L9 |
| C38 | 1000 PF | R20 | 2.00K | U5 | 22100 |
| C39 | 1000 PF | R21 | 47 | U6 | 22100 |
| C40 | 22 PF (FIG. 6) | R23 | 442K | U7 | TLC27L9 |
| C41 | 22 PF | R24 | 442K | U8 | TLC27L9 |
| C42 | 0.1 UF | R25 | 2.00K | U9 | TLC27L9 |
| C43 | 0.1 UF | R27 | 442K | U10 | TLC27L9 |
| C44 | 1000 PF | R28 | 200K | U11 | TLC27L9 |
| C45 | 1000 PF | R29 | 2.00K | U12 | TLC27L9 |
| CR2 | HSMS 2824 | R30 | 2.00K | U13 | TLC27L9 |
| CR3 | HSMS 2824 | R31 | 47 | U14 | TLC27M9 |
| CR4 | HSMS 2824 | R32 | 100K | U15 | TLC27L9 |
| D1 | FDSO 1503 | R33 | 100K | U16 | TLC27L9 |
| D2 | FDSO 1503 | R34 | 2.00K | U17 | TLC27L9 |
| D3 | HSMS 2822 | R35 | 47 | U18 | TLC27M9 |
| D4 | HSMS 2822 | R38 | 10.0K | U19 | TLC27M9 |
| D5 | HSMS 2822 | R39 | 2.00K | U20 | TLC27M9 |
| D6 | HSMS 2822 | R40 | 10K | U21 | TLC27M9 |
| D7 | HSMS 2822 | R41 | 2.00K | U22 | TLC27M9 |

-continued

| COMPONENT LISTING | | | | | |
|---|---|---|---|---|---|
| D8 | HSMS 2822 | R42 | 47 | U23 | TLC27M9 |
| | | R43 | 47 | U24 | TLC27M9 |
| | | R45 | 5.6K | U25 | ICL 7665 |
| | | R46 | 2.4K | U26 | TL061 |
| | | R47 | 120K | | |
| | | R48 | 2.7K | | |
| | | R49 | 51K | | |

While only a single embodiment of the invention has been illustrated and described, it is not intended to be limited thereby but only by the scope of the abandoned claims.

I claim:

1. A patient monitoring system for monitoring a patient at a first location and including a monitor and a central station receiver located at a second location remote from the first location, said monitor including signal generating means, means for coupling said signal generating means to patient leads so that said signal generating means may be connected to a patient at the first location for sensing individual ECG voltage signals, said signal generating means comprising means for generating ECG signals functionally related to the individual ECG voltage signals, digitizing means coupled to said signal generating means for digitizing means for receiving said digitized signals and for serializing the same, transmitting means for transmitting an RF signal and including oscillator means for generating an RF carrier signal and phase modulating means for phase modulating means being coupled to said oscillator means for receiving said RF carrier signal and to said control means for receiving said digital serialized ECG signals and comprising means for phase modulating said RF carrier signal with the serialized ECG signals, said transmitting means further comprising means for transmitting the phase modulated RF carrier signals by far field electromagnetic transmission from the first patient location to said central station receiver located at the second location.

2. The patient monitoring system set forth in claim 1 wherein said digitizing means comprises means for converting said analog signals into binary coded signals, said modulating means further comprising means for phase shifting said RF carrier signal through a first angle in response to a first binary signal received and through a second angle in response to a different binary signal received.

3. The patient monitoring system set forth in claim 2 wherein said first angle is 180 degrees and said second angle is zero degrees.

4. The patient monitoring system set forth in claim 3 wherein said control means includes analog to digital converter means connected to the differential means for receiving analog signals therefrom and to said control means and microprocessor means coupled to said analog to digital converter means for receiving digital signals from the analog to digital converter means representative of the analog ECG signals, said microprocessor means being operative to provide ECG signals serially to the modulating means.

5. The patient monitoring system set forth in claim 4 wherein said signal generating means comprises differential means for generating a signal functionally related to the difference between two received signals, a plurality of input terminal means for being coupled to a patient lead, at least one selected pair of input terminal means being coupled to said differential means for providing a pair of ECG voltage signals so that said differential means generates a differential signal functionally related to the difference between the selected pair of received ECG voltage signals.

6. The patient monitoring system set forth in claim 1 wherein said digitizing means further comprises means for converting said analog signals into binary coded signals, said modulating means including means for providing a 180° phase shift relative to said carrier signal in response to a first binary digit received and a zero degree phase shift relative to said carrier signal in response to a different binary digit received.

7. The patient monitoring system set forth in claim 6 and including lead fail signal generating means coupled to each of said leads for generating lead fail signals when any of said leads fail, said digitizing means also being coupled to said lead fail signal generating means for digitizing said lead fail signal, said control means also being coupled to received said digitized lead fail signals and for serializing said digitized lead fail signals with said serialized ECG signals and for providing the same to said phase signal modulating means.

8. The patient monitoring system set forth in claim 6 and including battery means for driving said control means and said transmitting means, low voltage sensing means coupled to said battery means for generating a low battery signal when the voltage output level of the battery falls below a predetermined value, said control means being coupled to said low voltage sensing means for receiving said low battery signal and being operative upon the receipt thereof to provide a low battery signal to the modulating means in series with the ECG vector signals and the lead fail signals.

9. The patient monitoring system set forth in claim 6 wherein there are at least four lead means for connecting respectively to the right arm, the left arm, the left leg and the chest, said differential means comprising first, second and third differential circuit means, said coupling means comprising means for connecting said first differential circuit means to receive said left leg and right arm signals, the second differential circuit means to receive said left leg and left arm signals, and said third differential circuit means to receive said chest and right arm, left arm, left leg signals, said differential circuit means further comprising means for providing ECG vector signals which are the difference between said signals received.

10. The patient monitoring system set forth in claim 6 and including means for detecting the existence of a pacemaker signal, said pacemaker signal detecting means also being coupled to said digitizing means, said control means also being coupled to the digitizing means for receiving the digital signal representative of the occurrence of a pacemaker signal, said control means being operative to provide said digitized representation of pacemaker signals to said modulating means in series with said ECG signal.

11. The patient monitoring system set forth in claim 10 wherein said digitizing means converts said analog signals into binary coded signals, said modulating means being operative to phase shift said carrier signal through a first angle in response to a first binary digit received and through a second angle in response to a different binary digit received.

12. The patient monitoring system set forth in claim 11 wherein said first angle is 180 degrees and said second angle is zero degrees.

13. The patient monitoring system set forth in claim 1 wherein said control means includes a microprocessor, said microprocessor including data storage means for storing said digital signals and serial data transfer means for transmitting said digital signals serially to the modulating means.

14. A method of cardiac monitoring comprising the steps of applying a plurality of patient leads to selected body sites of a patient at a first location, generating a plurality of analog voltage signals from said patient leads, selecting pairs of said analog voltage signals, generating a plurality of ECG vector signals from selected pairs of said analog voltage signals, digitizing said ECG vector signals, storing and serializing said digitized ECG vector signals, generating an RF carrier signal, phase modulating said RF carrier signal with the serialized ECG vector signals, transmitting by far field electromagnetic radiation and at radio frequencies the phase modulated RF carrier signals from the first location to a central station receiver located at a second location remote from the first location, and displaying the ECG vector signals at the second location.

15. The method set forth in claim 14 and including the step of converting said analog signals to binary coded signals, shifting the carrier signal through a first phase angle each time a first binary coded signal is received and phase shifting said carrier signal through a second phase angle each time a different binary coded signal is received.

16. The method set forth in claim 15 wherein said first angle is 180 degrees and said second angle is zero degrees.

17. The method set forth in claim 16 wherein said step of applying patient leads includes connecting a first lead means to the right arm, second lead means to the left arm, third lead means to the left leg, and a fourth means to the chest, producing a first lead couple vector signal from said left leg and right arm signals, a second lead couple vector signal from said left leg and left arm signals, and a third lead couple vector signal from the chest and right arm, left arm, left leg signals, digitizing each of said signals and phase modulating the carrier signal serially with said digitized signals.

18. The method set forth in claim 17 and including the step of detecting the existence of a pacemaker signal, providing a digital signal upon the occurrence of the pacemaker signal and phase modulating the carrier signal with the digital representation of the pacemaker signal in series with the ECG pair of vector signals.

19. The method set forth in claim 18 and including the steps of detecting the existence of a failure of one of said leads, providing a digital signal upon the occurrence of a lead failure, and phase modulating the carrier signal with the lead fail signal in series with the ECG vector pair of signals.

20. The method set forth in claim 19 and including the step of detecting the existence of a low battery condition, providing a digital signal upon the occurrence of a low battery signal, and phase modulating the carrier signal with the low battery digital signal in series with the ECG signals and the lead failure signals.

* * * * *